(12) United States Patent
Nakatani et al.

(10) Patent No.: US 8,303,920 B2
(45) Date of Patent: Nov. 6, 2012

(54) METHOD FOR REFINING DILUTION AIR AND DILUTION AIR REFINERY

(75) Inventors: Shigeru Nakatani, Kyoto (JP); Yoshinori Kato, Kyoto (JP); Tomomi Yamauchi, Tokyo (JP); Yoshitaka Iida, Tokyo (JP); Masato Koshikawa, Tokyo (JP)

(73) Assignee: Horiba, Ltd., Kyoto, Kyoto (JP)

( * ) Notice: Subject to any disclaimer, the term of this patent is extended or adjusted under 35 U.S.C. 154(b) by 73 days.

(21) Appl. No.: 12/948,170

(22) Filed: Nov. 17, 2010

(65) Prior Publication Data

US 2011/0117000 A1    May 19, 2011

(30) Foreign Application Priority Data

Nov. 18, 2009   (JP) .................. 2009-263335

(51) Int. Cl.
*B01D 53/34* (2006.01)
*B01D 53/56* (2006.01)
*B01D 53/86* (2006.01)
*G01N 31/22* (2006.01)
*G01N 35/00* (2006.01)

(52) U.S. Cl. .............. 423/210; 423/239.1; 422/168; 422/177; 422/83

(58) Field of Classification Search ............ 423/210, 423/239.1; 422/168, 177, 83
See application file for complete search history.

(56) References Cited

U.S. PATENT DOCUMENTS 5,756,360 A * 5/1998 Harvey et al. ............... 436/179
7,588,440 B2 * 9/2009 Smith ............................... 431/4

FOREIGN PATENT DOCUMENTS

| JP | 1994003232 | 1/1994 |
| JP | 1998019744 | 1/1998 |

* cited by examiner

*Primary Examiner* — Timothy Vanoy
(74) *Attorney, Agent, or Firm* — Brooks Kushman P.C.

(57) ABSTRACT

An object of this invention is to diminish a ratio of a concentration of $N_2O$ in the dilution air to a concentration of $N_2O$ in the measurement object gas diluted by the dilution air as much as possible by removing $N_2O$ in a dilution air so that a measurement accuracy of a concentration of $N_2O$ in a measurement object gas can be improved. A heater 33 that applies heat to the dilution air, a Pd catalyst 341 and a Pt catalyst 342 are arranged in this order on a flow channel where a dilution air used for diluting the measurement object gas flows, and $N_2O$ in the dilution air is oxidized to $NO_x$ or reduced to $N_2$ by the Pd catalyst 341 and the Pt catalyst 342.

7 Claims, 5 Drawing Sheets

| | | Flow rate [m³/min] | N₂O (ppm) | | | CH₄ | NMHC | THC | NO | NO₂ | NOₓ |
|---|---|---|---|---|---|---|---|---|---|---|---|
| | Temp.[°C] | | DAR inlet | DAR outlet | efficiency | | | | | | |
| EXPERIMENT EXAMPLE 1 | B.G. | | | | | 1.463 | 0.043 | 1.505 | 0.0013 | 0.0081 | 0.009 |
| | ① 360 | 7.5 | 0.32 | 0.30 | -5% | -0.027 | 0.052 | 0.027 | 0.0016 | 0.0004 | 0.0021 |
| | ② 360 | 14.6 | 0.27 | 0.09 | -67% | -0.018 | 0.056 | 0.036 | 0.0014 | 0.0014 | 0.0021 |
| | ③ 430 | 7.5 | 0.28 | 0.17 | -39% | -0.038 | 0.053 | 0.016 | 0.0102 | 0.001 | 0.0117 |
| | ④ 430 | 14.6 | 0.29 | 0.07 | -76% | -0.034 | 0.051 | 0.02 | 0.0112 | 0.0023 | 0.014 |
| | ⑤ 460 | 7.5 | | | | -0.038 | 0.055 | 0.017 | 0.0156 | 0.0002 | 0.0158 |
| EXPERIMENT EXAMPLE 2 | B.G. | | | | | 1.457 | 0.068 | 1.525 | 0.0087 | 0.0161 | 0.0244 |
| | B.G. | | | | | 1.516 | 0.08 | 1.596 | 0.0069 | 0.0164 | 0.023 |
| | ① 360 | 7.5 | 0.25 | 0.23 | -7% | -0.008 | 0.053 | 0.045 | 0.0022 | 0.0009 | 0.0029 |
| | ② 360 | 14.6 | 0.21 | 0.20 | -8% | 0.027 | 0.052 | 0.079 | 0.0017 | 0.0001 | 0.0014 |
| | ③ 430 | 7.5 | 0.20 | 0.07 | -66% | -0.003 | 0.057 | 0.024 | 0.0016 | 0.002 | 0.0036 |
| | ④ 430 | 14.6 | 0.22 | 0.14 | -39% | -0.035 | 0.066 | 0.032 | 0.0022 | 0.0017 | 0.0039 |
| | ⑤ 460 | 7.5 | 0.23 | -0.02 | -109% | -0.025 | 0.067 | 0.045 | 0.0044 | 0.0004 | 0.0047 |
| | ⑤' 460 | 7.5 | 0.23 | -0.01 | -103% | | | | | | |
| | ⑥ 460 | 14.6 | 0.22 | 0.09 | -59% | -0.019 | 0.054 | 0.036 | 0.0036 | 0.0005 | 0.0041 |
| | ⑦ 470 | 7.5 | 0.20 | -0.05 | -124% | -0.038 | 0.057 | 0.021 | 0.0029 | 0.0003 | 0.0031 |

FIG.4

METHOD FOR REFINING DILUTION AIR AND DILUTION AIR REFINERY

CROSS-REFERENCE TO RELATED APPLICATIONS

This application claims the benefit of JP 2009-263335, filed Nov. 18, 2009. The disclosure of which is incorporated in its entirety by reference herein.

FIELD OF THE ART

This invention relates to a method for refining a dilution air and a dilution air refinery that refines the dilution air used for diluting a measurement object gas such as an engine exhaust gas or the like.

BACKGROUND ART

Conventionally, as shown in the patent document 1 or the patent document 2, a dilution air refinery used for an analysis system of a measurement object gas such as an engine exhaust gas oxidizes CO, HC, $NO_x$ or the like by the use of an oxidation catalyst (Pd system, Pt system or the like) and adsorbs and removes $NO_x$ by an $NO_x$ remover.

Meanwhile, in order to remove HC, CO, $NO_x$ or the like in the exhaust gas, a Pt catalyst or a Pd catalyst (a three-way catalyst) is used, and purification of especially NO and CO is explained by a reaction of $2CO+2NO \rightarrow 2CO_2+N_2$ (reaction 1). However, depending on each catalytic condition such as concentration balance, it is known that a side reaction of $CO+2NO \rightarrow CO_2+N_2O$ (reaction 2) often happens and $N_2O$ is produced. After the reaction 2, when $CO+N_2O \rightarrow CO_2+N_2$ (reaction 3) is produced continuously, the reaction becomes equivalent to the above-mentioned reaction 1.

Recently, dinitrogen monoxide ($N_2O$) has drawn attention as a greenhouse gas. $N_2O$ contained in the exhaust gas is also no exception so that a need for analyzing a concentration of $N_2O$ contained in the exhaust gas arises.

In case that the exhaust gas sampling analysis system analyzes the exhaust gas by the use of a dilution sampling method, a concentration of a component in the dilution air is measured and a concentration of a component in the diluted exhaust gas is also measured, and a correction of a background is conducted by evaluating the difference between the measurement results, and finally a concentration of a component in the exhaust gas is calculated. The same method is used also in case of measuring a concentration of $N_2O$ in the exhaust gas.

However, $N_2O$ of about 300 [ppb] is already contained in the dilution air collected from the atmosphere. Then especially in case that the concentration of $N_2O$ contained in the exhaust gas is approximately equal to or less than 300 [ppb], there is a problem that the measurement accuracy of the concentration of $N_2O$ in the exhaust gas is aggravated because the measurement error of the concentration of $N_2O$ of the dilution air significantly affects a concentration of $N_2O$ in the exhaust gas after the correction of the background. In other words, there is a problem that a ratio of the concentration of $N_2O$ in the dilution air to the concentration of $N_2O$ in the diluted exhaust gas is big.

PRIOR ART DOCUMENT

Patent Document

Patent document 1: Japan patent laid-open number 6-3232
Patent document 2: Japan patent laid-open number 10-19744

SUMMARY OF THE INVENTION

Problems to be Solved by the Invention

This invention is attained as a result of a keen examination by the inventor of this invention by finding a layout and a condition of a catalyst appropriate for removing $N_2O$ in the dilution air and a main object of this invention is to improve the measurement accuracy of the concentration of $N_2O$ in the measurement object gas by removing $N_2O$ in the dilution air and diminishing a ratio of the concentration of $N_2O$ in the dilution air to the concentration of $N_2O$ in the measurement object gas diluted with the dilution air as much as possible.

Means to Solve the Problems

More specifically, a method for refining a dilution air in accordance with this invention is characterized by that a heater that heats the dilution air, a Pd catalyst containing Pd, a Pt catalyst containing Pt are arranged in this order on a flow channel where a dilution air used for diluting a measurement object gas flows, and $N_2O$ in the dilution air is oxidized to $NO_x$, or $N_2O$ in the dilution air is reduced to $N_2$ by the above-mentioned Pd catalyst and the Pt catalyst.

In accordance with this arrangement, since $N_2O$ is oxidized to $NO_x$ or reduced to $N_2$ by the Pd catalyst and the Pt catalyst, it is possible to remove $N_2O$ in the dilution air. As a result, it is possible to diminish a ratio of the concentration of $N_2O$ in the dilution air to the concentration of $N_2O$ in the measurement object gas diluted by the dilution air as much as possible so that a measurement accuracy of the concentration of $N_2O$ in the measurement object gas can be improved. From a viewpoint of a conventional technical common sense regarding the three-way catalyst, if the dilution air passes the Pd catalyst or the Pt catalyst, there is concern that $N_2O$ contained in the dilution air increases because $N_2O$ is newly produced by means of the above-mentioned reaction 2. However, as a result of a keen examination by the inventor of this invention by breaking away from the conventional common sense, the inventor has found that if the dilution air passes the Pd catalyst or the Pt catalyst, $N_2O$ contained in the dilution air is far from increasing, but traces (about 300 ppb) of $N_2O$ contained in the dilution air decreases.

At this time, the Pd catalyst containing Pd is superior to the Pt catalyst containing Pt in a reduction performance or an oxidation performance of $N_2O$. Since the dilution air passing the heater first contacts the Pd catalyst, it is possible to efficiently reduce or oxidize $N_2O$ in the dilution air. In addition, since the Pd catalyst is arranged on the upstream side and the Pt catalyst is arranged on the downstream side, the Pd catalyst locating on the upstream side mainly produces $CO+N_2O \rightarrow N_2+CO_2$ (reaction 3) so that a majority of $N_2O$ is reduced and removed. Meanwhile, since the Pt catalyst locating on the downstream side removes mainly hydrocarbon such as methane, and the Pt catalyst does not oxidize $N_2$ produced by the Pd catalyst to $N_2O$, $N_2O$ does not increase.

In order to promote oxidation of $N_2O$ to $NO_2$ or reduction of $N_2O$ to $N_2$ for the Pd catalyst, it is preferable that at least the Pd catalyst is controlled at a temperature greater than or equal to 430 degrees centigrade. In addition, if the Pd catalyst is heated too much, a life span of the Pd catalyst is shortened. As a result, it is preferable the Pd catalyst is controlled at a temperature between 430 degrees centigrade and 500 degrees centigrade. Furthermore, in order to further promote conversion, namely an oxidation reaction of $N_2O$ to $NO_2$ and the reduction reaction of $N_2O$ to $N_2$ by means of the Pd catalyst, it is preferable that the Pd catalyst is controlled at a temperature between 460 degrees centigrade and 470 degrees centigrade.

In addition, a dilution air refinery in accordance with this invention is a dilution air refinery that refines a dilution air used for diluting a measurement object gas, and is characterized by comprising a Pd catalyst that contains Pd and that is arranged on a flow channel where a dilution air collected from an atmosphere flows, and the Pd catalyst is controlled at a temperature greater than or equal to 430 degrees centigrade.

In accordance with this arrangement, since it is possible to promote the oxidation reaction of $N_2O$ in the dilution air to $NO_2$ or the reduction reaction of $N_2O$ in the dilution air to $N_2$ by controlling the Pd catalyst at the temperature greater than or equal to 430 degrees centigrade, it is possible to diminish a ratio of the concentration of $N_2O$ in the dilution air to the concentration of $N_2O$ in the exhaust gas diluted by the dilution air as much as possible by removing $N_2O$ in the dilution air so that the measurement accuracy of the concentration of $N_2O$ in the exhaust gas can be improved.

As a concrete embodiment not only for controlling the temperature of the catalyst but also for producing the oxidation reaction or the reduction reaction in a more optimal condition by controlling the temperature of the dilution air, it is preferable to comprise a heater that is arranged on the upstream of the Pd catalyst and that controls the dilution air collected from the atmosphere at a temperature greater than or equal to 430 degrees centigrade, a Pt catalyst that is arranged on the downstream of the Pd catalyst and that contains Pt oxidizing or reducing the dilution air, and an $NO_x$ adsorbent that is arranged on the downstream of the Pt catalyst and that adsorbs $NO_x$ produced by oxidizing $N_2O$ by means of the Pd catalyst and the Pt catalyst.

Effect of the Invention

In accordance with this invention of the above arrangement, it is possible to diminish a ratio of the concentration of $N_2O$ in the dilution air to the concentration of $N_2O$ in the exhaust gas diluted by the dilution air as much as possible by removing $N_2O$ in the dilution air so that a measurement accuracy of the concentration of $N_2O$ in the exhaust gas can be improved.

BRIEF DESCRIPTION OF THE DRAWINGS

FIG. 4 is an experimental result showing a removing efficiency of $N_2O$ by the catalytic device.

MODES OF EMBODYING THE INVENTION

One embodiment of an exhaust gas sampling analysis system using a dilution air refinery in accordance with this invention will be explained with reference to drawings.

The exhaust gas sampling analysis system 100 in accordance with this embodiment is of a dilution sampling method. The exhaust gas sampling analysis system 100 several fold dilutes the engine exhaust gas (hereinafter called as "exhaust gas") collected from an automobile 200 with a dilution air refined from an atmospheric air and measures a concentration of the diluted exhaust gas. In this embodiment explained is a constant volume dilution sampling method wherein all of the exhaust gas is sampled and diluted with the dilution air so as to make a certain given flow rate.

Figure 1:
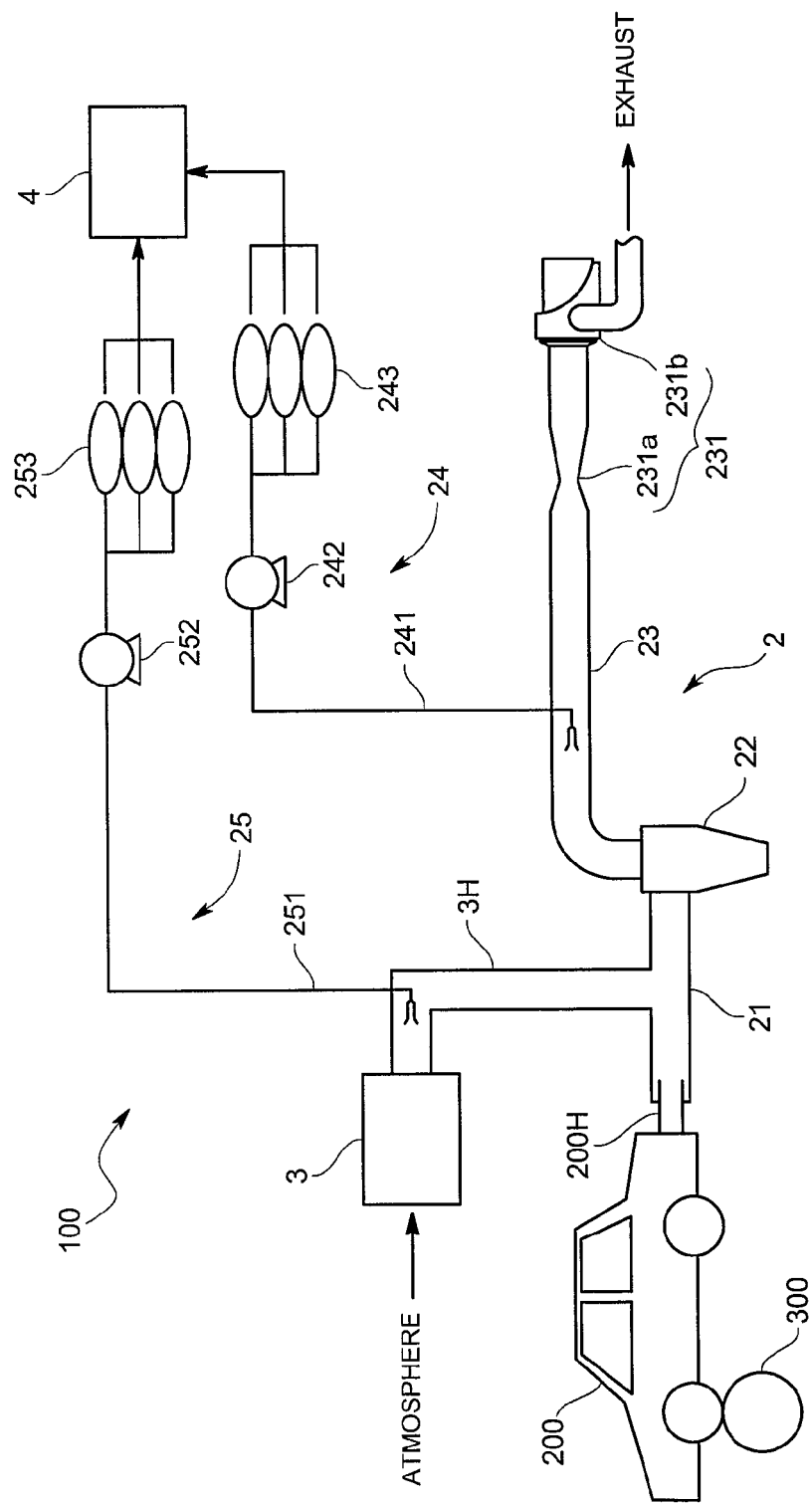
FIG. 1 is a pattern perspective view of an exhaust gas sampling analysis system of one embodiment of this invention.

Concretely, the exhaust gas sampling analysis system 100 comprises, as shown in FIG. 1, a constant volume sampling device 2 that introduces all of the exhaust gas and the dilution air into the constant volume sampling device 2 and that controls the total flow rate of the exhaust gas and the dilution air to be constant so that a part of the diluted exhaust gas (hereinafter called as "the diluted exhaust gas) is collected at a constant flow rate into a collection bag, a dilution air refinery 3 that supplies the constant volume sampling device 2 with the dilution air that is refined by removing impure substances from the atmospheric air and a gas analyzer 4 that analyzes a concentration of a predetermined component (for example, HC, CO, $H_2O$, CO, $NO_x$, $N_2O$ or the like) in the diluted exhaust gas collected into the collection bag of the constant volume sampling device 2.

The constant volume sampling device 2 is connected to an exhaust pipe 200H of an automobile 200 that is mounted on a chassis dynamo 300. The constant volume sampling device 2 comprises an exhaust gas introduction line 21 to which a dilution air supply pipe 3H of the dilution air refinery 3 is introduced and connected, a cyclone 22 that is arranged on the downstream of the exhaust gas introduction line 21 and that agitates and mixes the exhaust gas and the dilution air, a diluted exhaust gas circulation line 23 having a constant flow rate mechanism 231 that flows the diluted exhaust gas agitated and mixed by the cyclone 22 at a constant flow rate, a diluted exhaust gas collection line 24 that collects a part of the diluted exhaust gas from the diluted exhaust gas circulation line 23 and a dilution air collection line 25 that collects a part of the dilution air from the dilution air supply pipe 3H of the dilution air refinery 3.

The constant flow rate mechanism 231 comprises a venturi tube 231a arranged on the diluted exhaust gas circulation line 23 and a turbo blower 231b arranged on the downstream of the venturi tube 231a.

The diluted exhaust gas collection line 24 comprises a diluted exhaust gas collection pipe 241 whose one end is arranged in the diluted exhaust gas circulation line 23, and a diluted exhaust gas collection pump 242 arranged on the diluted exhaust gas collection pipe 241 and a diluted exhaust gas bag 243 that houses the diluted exhaust gas collected by the diluted exhaust gas collection pump 242. The diluted exhaust gas collection pipe 241 is arranged on the upstream side of the constant flow rate mechanism 231.

In addition, the dilution air collection line 25 comprises a dilution air collection pipe 251 whose one end is arranged in the dilution air supply pipe 3H, a dilution air collection pump 252 arranged on the dilution air collection pipe 251 and a dilution air bag 253 that houses the dilution air collected by the dilution air collection pump 252.

Then so-called a bag measurement is conducted by the gas analyzer 4 by the use of the diluted exhaust gas bag 243 of the diluted exhaust gas collection line 24 and the dilution air bag 253 of the dilution air collection line 25.

The dilution air refinery 3 removes CO, HC, $NO_x$, $N_2O$ or the like in the dilution air in order to stabilize a background in analyzing the exhaust gas at a low concentration. For the dilution air refinery 3, a method for removing CO, HC, NO, $N_2O$ is to convert CO, HC, NO, $N_2O$ in the dilution air to $CO_2$, $H_2O$, $N_2$, $NO_2$, and to conduct an adsorptive treatment on $NO_2$ produced by means of oxidization of NO, $N_2O$ by the use of an $NO_x$ adsorbent. Furthermore, the $NO_x$ adsorbent also contains an oxidizing reagent and an adsorptive treatment is conducted by oxidizing unconverted NO to $NO_x$.

Figure 2:
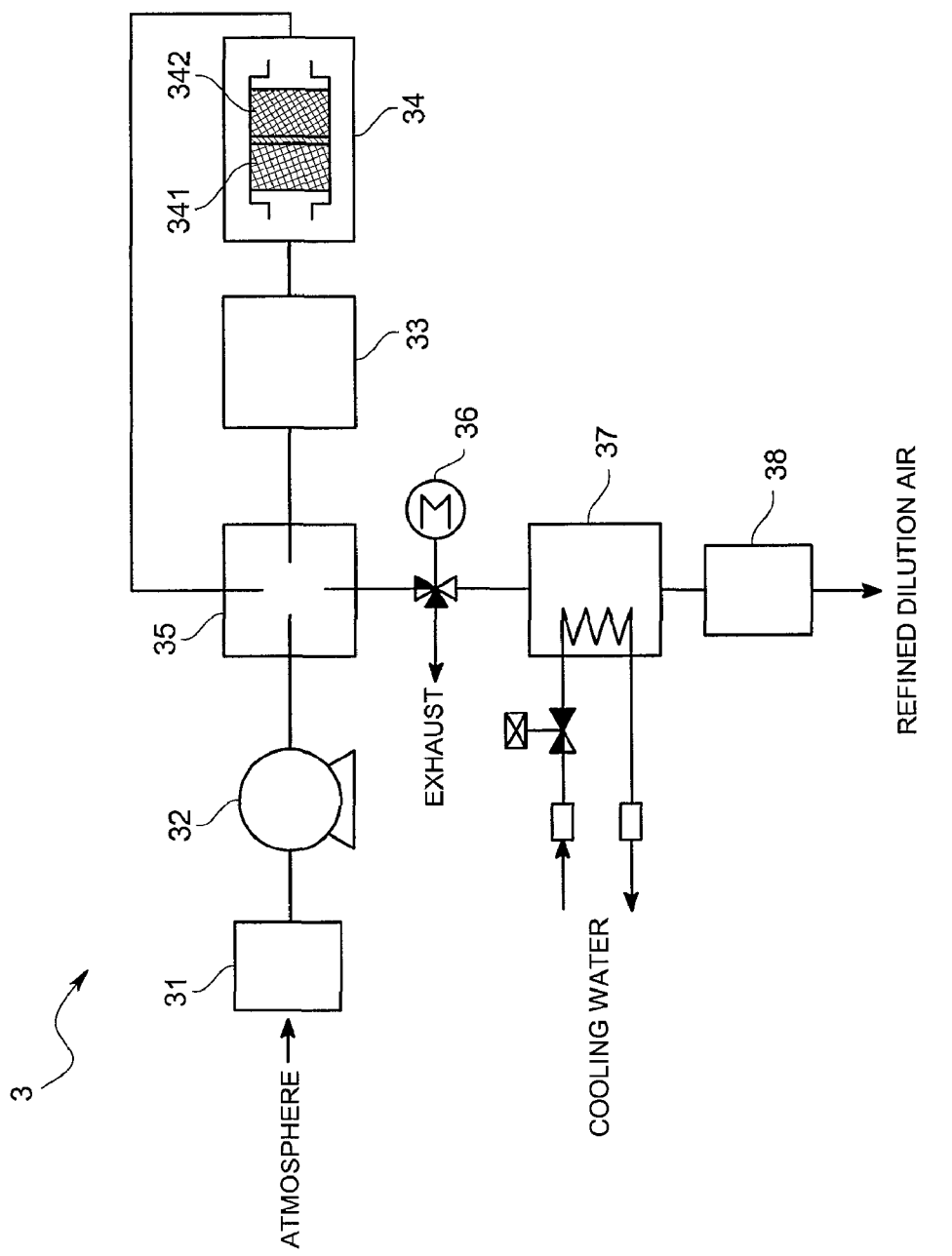
FIG. 2 is a view showing a configuration of a dilution air refinery of this embodiment.

As a concrete structure, the dilution air refinery 3 comprises, as shown in FIG. 2, a suction pump 32 that introduces the dilution air from outside to inside of the dilution air refinery 3 through a sucking filter 31, a heater 33 that heats the dilution air introduced by the suction pump 32 at a predetermined temperature, a catalytic device 34 that converts HC, CO, $NO_x$, $N_2O$ or the like in the dilution air heated by the heater 33 to $CO_2$, $H_2O$, $NO_2$, $N_2$ or the like, a cooler 37 that cools the dilution air passing the catalytic device 34, a heat exchanger 35 and a three-way solenoid valve 36 arranged downstream of the catalytic device 34, and an $NO_x$ adsorber 38 as being an $NO_x$ removing part that adsorbs and removes $NO_2$ in the dilution air cooled at, for example, 25 degrees centigrade by the cooler 37. Then the dilution air passing the $NO_x$ adsorber 38 is supplied to the constant volume sampling device 2 through the dilution air supplying pipe 3H.

The heater 33 is to apply heat to the dilution air collected from the atmosphere at 430 degrees centigrade or over so as to make the dilution air flow into a Pd catalyst 341, to be described later, of the catalytic device 34 at the above-mentioned temperature.

The catalytic device 34 is so arranged that the Pd catalyst 341 containing Pd and a Pt catalyst 342 containing Pt are arranged in this order from the upstream on the flow channel where the dilution air collected from the atmosphere flows. The Pd catalyst 341 comprises Pd supported by a porous supporting body such as zeolite powders, activated carbon, aluminum oxide or the like, and the Pt catalyst 342 comprises Pt supported by zeolite powders.

Furthermore, the Pd catalyst 341 and the Pt catalyst 342 are heated at 430 degrees centigrade or over by a heating mechanism, not shown in drawings. If the Pd catalyst 341 is heated too much, a function of the Pd catalyst as a catalyst drops. As a result, the Pd catalyst 341 is controlled at a temperature between 430 degrees centigrade and 500 degrees centigrade in this embodiment. Furthermore, in order to further promote conversion of $N_2O$ by means of oxidation to $NO_2$ and by means of reduction to $N_2$ by the Pd catalyst 341, the Pd catalyst 341 is controlled at a temperature between 460 degrees centigrade and 470 degrees centigrade. The heater 33 applies heat to the dilution air at a temperature generally equal to the temperature of the Pd catalyst 341. In addition, since the Pt catalyst 342 is integrally arranged with the Pd catalyst 341, the Pt catalyst is also heated at a temperature generally equal to that of the Pd catalyst by means of the heating mechanism.

Figure 3:
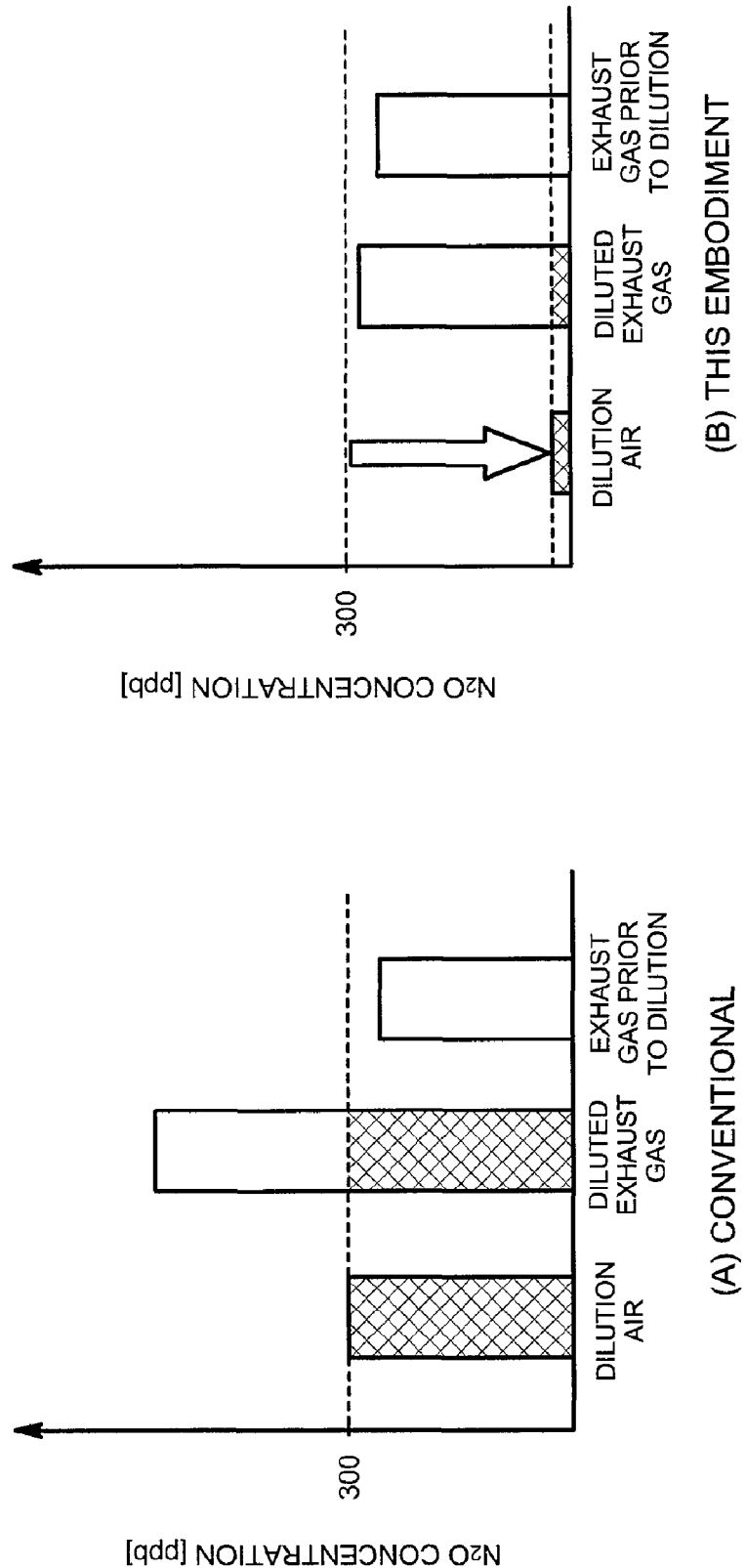
FIG. 3 is a pattern diagram showing a correction result with or without removing $N_2O$ in the dilution air.

Next, a measurement of a concentration of $N_2O$ by the use of the exhaust gas sampling analysis system 100 having the above-mentioned arrangement will be explained with reference to FIG. 3.

In case that an $N_2O$ removing function is not provided for the dilution air refinery 3, the concentration of $N_2O$ in the dilution air obtained from the dilution air bag 253 is about 300 [ppb] (an average value of the concentration of $N_2O$ contained in the atmosphere). At this time, if the concentration of $N_2O$ in the diluted exhaust gas obtained from the diluted exhaust gas bag 243 is about 560 [ppb], the concentration of $N_2O$ contained in the exhaust gas becomes about 260 [ppb] as a result of a correction of the background. However, a ratio of the concentration of $N_2O$ in the dilution air to the concentration of $N_2O$ in the diluted exhaust gas becomes big so that an influence of the measurement error of the concentration of $N_2O$ in the dilution air on the concentration of $N_2O$ in the exhaust gas becomes significant. As a result, a measurement accuracy of the concentration of $N_2O$ in the exhaust gas obtained after the correction of the background drops.

Meanwhile, if the concentration of $N_2O$ in the dilution air obtained from the dilution air bag 253 is reduced to, for example, about 30 [ppb] by arranging an $N_2O$ removing function like this embodiment, the concentration of $N_2O$ in the diluted exhaust gas obtained from the diluted exhaust gas bag 243 becomes about 290 [ppb]. Then as a result of the correction of the background, the concentration of $N_2O$ contained in the exhaust gas becomes about 260 [ppb]. At this time, the ratio of the concentration of $N_2O$ in the dilution air to the concentration of $N_2O$ in the diluted exhaust gas can be diminished so that it is possible to diminish an influence of the measurement error of the concentration of $N_2O$ in the dilution air on the concentration of $N_2O$ in the exhaust gas. As a result, it is possible to improve the measurement accuracy of the concentration of $N_2O$ in the exhaust gas obtained as a result of the correction of the background.

Next, for both cases of a catalytic device wherein a Pt catalyst and a Pd catalyst are arranged in this order from the upstream and of the catalytic device (of this embodiment) wherein the Pd catalyst 341 and the Pt catalyst 342 are arranged in this order from the upstream, efficiencies of removing $N_2O$ in case of changing a heated temperature of the dilution air, the Pd catalyst and the Pt catalyst will be explained.

An experimental example 1 is a case that the catalytic device wherein the Pt catalyst and the Pd catalyst are arranged in this order from the upstream is used and the catalytic device and the dilution air are heated at 360 degrees centigrade, 430 degrees centigrade, and 460 degrees centigrade and a flow rate of the dilution air at each temperature is set 7.5 [m$^3$/min] and 14.6 [m$^3$/min].

Meanwhile, an experimental example 2 is a case that the catalytic device 34 wherein the Pd catalyst 341 and the Pt catalyst 342 are arranged in this order from the upstream is used and the catalytic device 34 and the dilution air are heated at 360 degrees centigrade, 430 degrees centigrade, and 460 degrees centigrade and a flow rate of the dilution air at each temperature is set 7.5 [m$^3$/min] and 14.6 [m$^3$/min].

For each of the cases, an effect of removing $N_2O$ by the use of the catalytic device is obtained by measuring the concentration of $N_2O$ at an inlet (DAR inlet) of the dilution air refinery 3 and the concentration of $N_2O$ at an outlet (DAR outlet) of the dilution air refinery 3.

Figure 5:
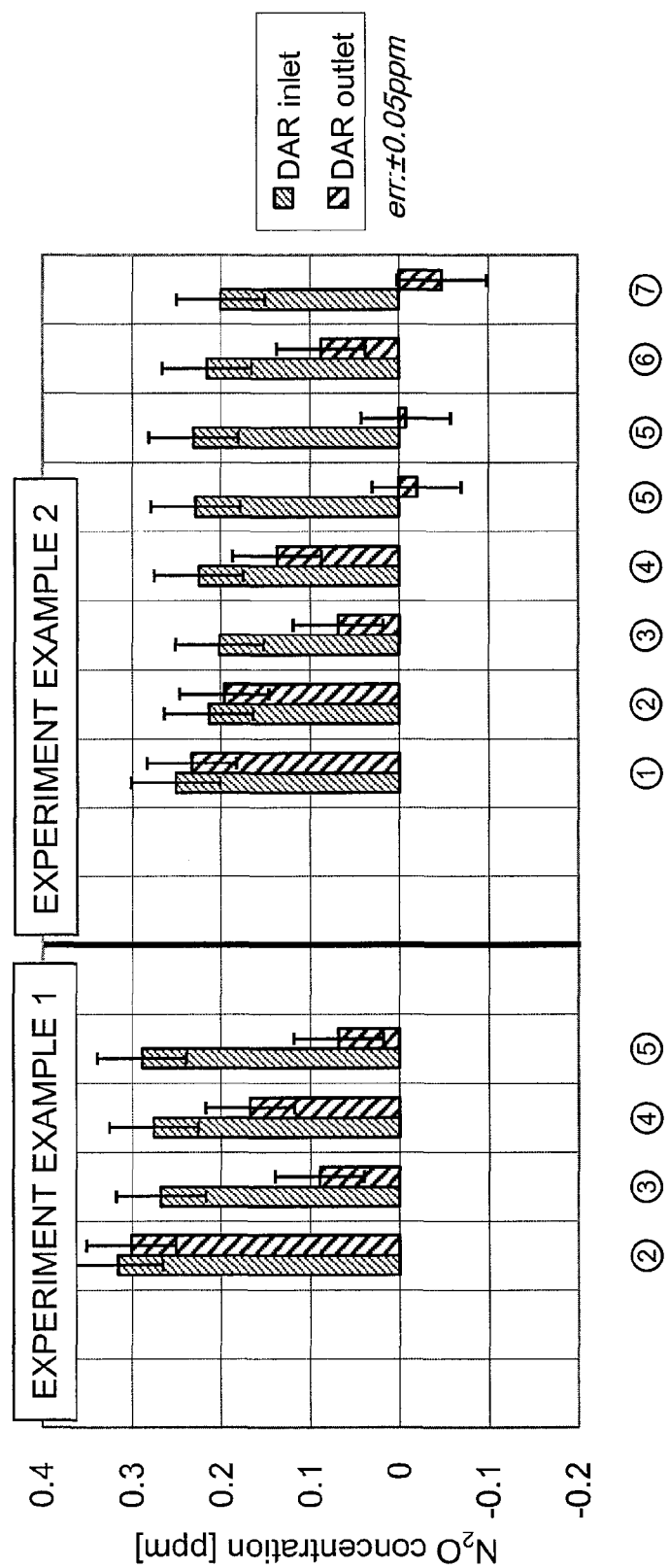
FIG. 5 is a graph showing the removing efficiency of $N_2O$ by the catalytic device.

As is clear from FIG. 4 and FIG. 5, in case that the catalytic device is heated at 430 degrees centigrade or over for the experimental example 1, an effect of reducing $N_2O$ is significantly improved. Due to an Sv value [1/hr] (=a processed gas volume [m$^3$ hr]/a catalyzed volume [m$^3$]) of the catalytic device, if the flow rate of the dilution air becomes big, an effect of removing $N_2O$ drops.

In addition, in case that the catalytic device 34 is heated at 430 degrees centigrade or over for the experimental example 2, it is turned out that the effect of reducing $N_2O$ is significantly improved, and especially at 460 degrees centigrade and 470 degrees centigrade, the $N_2O$ reducing effect is remarkable. In case that the heated temperature is at 460 degrees centigrade and the flow rate of the dilution air is 7.5 [m$^3$/min], the removing efficiency showing over 100% is due to a measurement error. In case of the experimental example 2, hydrocarbon such as methane is reduced mainly by the Pt catalyst 342. In addition, it is considered that a case of arranging the Pd catalyst on the upstream side and the Pt catalyst on the downstream side (the experimental example 2) is better than a case of arranging the Pt catalyst on the upstream side and the Pd catalyst on the downstream side (the experimental example 1) in a balance between the above-mentioned reaction 2 and the reaction 3 and more efficient in removing $N_2O$.

<Effect of this Embodiment>

In accordance with the exhaust gas sampling analysis system 100 of this embodiment, since it is possible to diminish a ratio of the concentration of $N_2O$ in the dilution air to the concentration of $N_2O$ in the diluted exhaust gas as much as possible by removing $N_2O$ from the dilution air before diluting the exhaust gas with the dilution air, the measurement accuracy of the concentration of $N_2O$ in the exhaust gas can be improved by diminishing a fluctuation of the background of the concentration of $N_2O$.

At this time, since the heater 33, the Pd catalyst 341 and the Pt catalyst 342 are arranged in this order from the upstream on the flow channel where the dilution air flows, the dilution air passing the heater 33 first contacts the Pd catalyst 341 so that $N_2O$ in the dilution air can be oxidized efficiently. Meanwhile, since the Pt catalyst 342 is arranged at a position separated from the heater 33, the temperature of the dilution air that contacts the Pt catalyst 342 drops so that $N_2O$ produced by the Pt catalyst 342 can be restrained as much as possible.

In addition, it is possible to promote the oxidation reaction of $N_2O$ in the dilution air to $NO_2$ or the reduction reaction of $N_2O$ to $N_2$ by controlling the Pd catalyst at 430 degrees centigrade or over.

The present claimed invention is not limited to the above-mentioned embodiment.

For example, in the above-mentioned embodiment, the constant volume sampling device is used, however, a bag mini dilutor that collects a part of the exhaust gas and dilutes it at a constant ratio may be used.

In addition, the temperature of the dilution air heated by the heater and the temperature of the Pd catalyst heated by the heating mechanism is generally the same in the above-mentioned embodiment, however, each of the temperature may be adjusted in consideration of the influence of the temperature due to piping.

Furthermore, the Pd catalyst and the Pt catalyst in the above-mentioned embodiment are integrally formed by the use of a partition member, however, the Pd catalyst and the Pt catalyst may be formed individually. At this time, a heater may be arranged on the upstream of the Pd catalyst and the Pt catalyst respectively and the temperature of the dilution air flowing into each catalyst may be adjusted or the temperature of each catalyst may be adjusted independently.

In addition, the Pd catalyst is arranged on the upstream side and the Pt catalyst is arranged on the downstream side in the above-mentioned embodiment, however, the Pt catalyst may be arranged on the upstream side and the Pd catalyst may be arranged on the downstream side. In case that the Pd catalyst is arranged on the downstream side, it is possible to obtain the same effect as that of the above-mentioned embodiment if the Pd catalyst is heated at 430 degrees centigrade or over.

The present claimed invention is not limited to the above-mentioned embodiment and it is a matter of course that it may be variously modified without departing from a spirit of the invention.

EXPLANATION OF CODE

100 . . . exhaust gas sampling analysis system
2 . . . constant volume sampling device
3 . . . dilution air refinery
33 . . . heater
34 . . . catalytic device
341 . . . Pd catalyst
342 . . . Pt catalyst
38 . . . $NO_X$ removing part

The invention claimed is:

1. A method for refining a dilution air wherein
on a flow channel where a dilution air used for diluting a measurement object gas flows arranged are a heater that heats the dilution air, a Pd catalyst having Pd, a Pt catalyst having Pt in this order, and
$N_2O$ in the dilution air is oxidized to $NO_X$, or $N_2O$ in the dilution air is reduced to $N_2$ by the above-mentioned Pd catalyst and the Pt catalyst.

2. The method for refining a dilution air described in claim 1, wherein
at least the Pd catalyst is controlled at a temperature greater than or equal to 430 degrees centigrade.

3. A dilution air refinery that refines a dilution air used for diluting a measurement object gas, wherein comprising
a Pd catalyst that contains Pd and that is arranged on a flow channel where a dilution air collected from an atmosphere flows, and the Pd catalyst is controlled at a temperature greater than or equal to 430 degrees centigrade.

4. The dilution air refinery described in claim 3, wherein comprising
a heater that is arranged on the upstream of the Pd catalyst and that controls the dilution air collected from the atmosphere at a temperature greater than or equal to 430 degrees centigrade,
a Pt catalyst that is arranged on the downstream of the Pd catalyst and that contains Pt oxidizing or reducing the dilution air, and
an $NO_X$ removing part that is arranged on the downstream of the Pt catalyst and that adsorbs $NO_X$ produced by oxidizing $N_2O$ by means of the Pd catalyst and the Pt catalyst.

5. A method for refining a dilution air wherein on a flow channel where a dilution air used for diluting a measurement object gas flows arranged are a heater that heats the dilution air, a Pd catalyst having Pd, a Pt catalyst having Pt, and $N_2O$ in the dilution air is oxidized to $NO_X$, or $N_2O$ in the dilution air is reduced to $N_2$ by the above-mentioned Pd catalyst and the Pt catalyst.

6. An exhaust gas sampling analysis system using the method for refining a dilution air as described in claim 5.

7. An exhaust gas sampling analysis system using the dilution air refinery as described in claim 3.

* * * * *